United States Patent
Hashimoto et al.

(10) Patent No.: US 8,536,084 B2
(45) Date of Patent: Sep. 17, 2013

(54) PHOTOCATALYST MATERIAL, METHOD FOR DECOMPOSITION OF ORGANIC MATERIAL, INTERIOR MEMBER, AIR PURIFICATION DEVICE, AND APPARATUS FOR PREPARATION OF OXIDIZING AGENT

(75) Inventors: Kazuhito Hashimoto, Sakae-ku (JP); Hiroshi Irie, Kofu (JP); Syuhei Miura, Shibuya-ku (JP); Kazuhide Kamiya, Shibuya-ku (JP); Shinichiro Miki, Osaka (JP); Koichi Takahama, Amagasaki (JP); Mitsuo Yaguchi, Ibaraki (JP)

(73) Assignees: The University of Tokyo, Tokyo (JP); Panasonic Corporation, Kadoma-shi (JP)

( * ) Notice: Subject to any disclaimer, the term of this patent is extended or adjusted under 35 U.S.C. 154(b) by 290 days.

(21) Appl. No.: 12/736,209

(22) PCT Filed: Mar. 19, 2009

(86) PCT No.: PCT/JP2009/055452
§ 371 (c)(1),
(2), (4) Date: Sep. 20, 2010

(87) PCT Pub. No.: WO2009/116627
PCT Pub. Date: Sep. 24, 2009

(65) Prior Publication Data
US 2011/0005916 A1      Jan. 13, 2011

(30) Foreign Application Priority Data
Mar. 21, 2008   (JP) .................. 2008-073930

(51) Int. Cl.
*B01J 23/888* (2006.01)
*A61L 2/08* (2006.01)
*B32B 19/00* (2006.01)

(52) U.S. Cl.
USPC ........... 502/318; 422/186.3; 422/22; 428/701

(58) Field of Classification Search
USPC ................ 422/121, 186.3, 22; 502/331, 318; 428/701
See application file for complete search history.

(56) References Cited

U.S. PATENT DOCUMENTS 5,817,427 A * 10/1998 Ishida et al. ............... 428/537.5
8,173,573 B2   5/2012 Nakano et al.
(Continued)

FOREIGN PATENT DOCUMENTS

CN   2339914 Y   9/1999
EP   2248586 A1   11/2010
(Continued)

OTHER PUBLICATIONS

P. Maruthamuthu et al., "Hydrogen evolution from water with visible radiation in presence of Cu(II)/WO$_3$ and electron relay," International Journal of Hydrogen Energy, Elsevier Science Publishers B.V., Barking, GB, vol. 14, No. 8, Jan. 1, 1989, pp. 525-528.

(Continued)

*Primary Examiner* — Kishor Mayekar
(74) *Attorney, Agent, or Firm* — Edwards Wildman Palmer LLP

(57) ABSTRACT

The present invention provides a tungsten trioxide microparticle carrying on its surface divalent copper salt. The divalent copper salt is utilized to perform a multi-electron reduction of oxygen. The tungsten trioxide exhibits a high oxidative decomposition activity when exposed to visible light.

10 Claims, 2 Drawing Sheets

(56) References Cited

U.S. PATENT DOCUMENTS

| | | | |
|---|---|---|---|
| 2004/0197300 A1 | 10/2004 | Nonami | |
| 2010/0190633 A1* | 7/2010 | Bai et al. ................ | 502/63 |
| 2010/0292075 A1 | 11/2010 | Nakano et al. | |

FOREIGN PATENT DOCUMENTS

| | | |
|---|---|---|
| JP | 09-192496 A | 7/1997 |
| JP | 2003-012306 A | 1/2003 |
| JP | 2004-000988 A | 1/2004 |
| JP | 3601532 | 1/2004 |
| JP | 2007-228233 A | 9/2007 |
| JP | 2008-149312 A | 7/2008 |

OTHER PUBLICATIONS

P. Maruthamuthu et al., "Hydrogen generation using Cu(II)/$WO_3$ and oxalic acid by visible light," International Journal of Hydrogen Energy, Elsevier Science Publishers B.V., Barking, GB, vol. 13, No. 11, Jan. 1, 1988, pp. 677-680.

H. Irie et al., "Efficient visible light-sensitive photocatalysts: Grafting Cu(II) ions onto $TiO_2$ and $WO_3$ photocatalysts," Chemical Physics Letters, Elsevier BV, NL, vol. 457, No. 1-3, May 20, 2008, pp. 202-205.

Supplementary European Search Report dated Jan. 3, 2012, issued for the European patent application No. 09721400.1.

Cai, R. et al, "Effect of copper ions on the formation of hydrogen peroxide from photocatalytic titanium dioxide particles," Journal of Catalysis, 2003, vol. 219, Issue 1, pp. 214-218.

Arai, T. et al, "Promotion effect of CuO co-catalyst on $WO_3$-catalyzed photodegradation of organic substances," Catalysis Communications, 2008, vol. 9, No. 6, pp. 1254-1258.

Arai, T. et al, "The enhancement of $WO_3$-catalyzed photodegradation of organic substances utilizing the redox cycle of copper ions," Applied Catalysis B: Environmental, 2008, vol. 84, No. 1-2, pp. 42-47.

International Search Report dated Jun. 16, 2009, issued in PCT/JP2009/055452.

M. Ashokkumar et al., "Preparation and characterization of doped $WO_3$ photocatalyst powders," Journal of Materials Science Letters 24, 1989, pp. 2135-2139.

Office Action dated Mar. 1, 2013, issued for the corresponding European Application No. 09 721 400.1.

Office Action mailed Dec. 11, 2012, issued for the Japanese counterpart application No. 2008-073930.

\* cited by examiner

PHOTOCATALYST MATERIAL, METHOD FOR DECOMPOSITION OF ORGANIC MATERIAL, INTERIOR MEMBER, AIR PURIFICATION DEVICE, AND APPARATUS FOR PREPARATION OF OXIDIZING AGENT

TECHNICAL FIELD

This invention relates to visible light-activated photocatalyst materials, methods for decomposition of organic materials by using the photocatalyst materials, as well as interior members, air purification devices, and apparatus for preparation of oxidizing agents which are respectively formed of the photocatalyst materials.

BACKGROUND ART

Recently, many studies have been carried out to develop various photocatalyst materials for application to environmental cleaning, odor elimination, dirt elimination, sterilization, and so on. Such a photocatalyst material is designed to utilize a less costly light with a significantly reduced environmental load as an energy source for oxidatively decomposing organic materials and inorganic materials (e.g., nitrogen oxides).

Titanium oxide has been widely known as a photocatalyst which exhibits an activity when exposed to UV-ray. The photocatalyst material has been studied and developed to meet requirements for utilized in interior of house and circumstances hardly exposed to UV-ray. For example, patent reference 1 (Japanese patent publication No. 3601532) discloses a photocatalyst material exhibiting visible-light activity in which oxygen atom sites of titanium oxide crystal are partially substituted with nitrogen atoms.

In the photocatalyst material of patent reference 1, oxygen atom sites of titanium oxide crystal are partially substituted with nitrogen atoms to form a new isolated level in a bandgap of titanium oxide, for having the visible-light activity. When being exposed to photons each having an energy larger than a bandgap energy of titanium oxide, electrons in the isolated level are excited to the conduction band of titanium oxide, leaving holes in the isolated level for exhibiting activation.

However, the isolated level formed in the bandgap of titanium oxide has a small electronic potential, thereby generating poorly oxidizing holes resulting from photoexcitation of electrons by exposure to visible light. Besides, the holes in the isolated level is restricted from freely migrating, exhibiting a poor reactivity to oxidized substrates. Accordingly, the photocatalyst material in the patent reference 1 exhibits a poor oxidative decomposition activity, albeit having visible-light activity.

Tungsten trioxide has a large electronic potential in its valence band (3.1 to 3.2 V vs. SHE, pH=0), thereby holes generated by photoirradiation is highly oxidative. Tungsten trioxide has an electronic potential of 0.3 to 0.5 V (3.1 to 3.2 V vs. SHE, pH=0) at the bottom of its conduction band, thereby being widely known as a photocatalyst material having a visible-light activity.

However, the electronic potential at the bottom of the conduction band is larger than one-electron reduction potential of oxygen (−0.046 V vs. SHE, pH=0), thereby not enabling photoexcited electrons to perform one-electron reduction of oxygen atoms. The photoexcited electrons are recombined to the generate holes, and are utilized to reduce W (VI) of tungsten trioxide to W (V) for exhibiting photochromism, leading to a lowered oxidative decomposition activity. Accordingly, tungsten trioxide exhibits a significantly poor oxidative decomposition activity.

The present invention has been accomplished in view of the above problems, and has an object to provide a photocatalyst material comprising a tungsten trioxide which is activated by irradiation of visible light to exhibit a high oxidative decomposition activity. The present invention also has an object to provide a method for decomposition of organic materials, an interior member, an air-purification device, and an apparatus for preparation of an oxidizing agent by utilizing the high oxidative decomposition activity.

DISCLOSURE OF THE INVENTION

The present invention is characterized by a visible light-activated photocatalyst material comprising a tungsten trioxide microparticle carrying on its surface a divalent copper salt.

The divalent copper salt carried on the tungsten trioxide has a copper content of 0.0001% to 1% by weight of tungsten trioxide. The divalent copper salt is preferably composed of hydroxide anion.

In the present invention, the divalent copper salt is utilized as a catalyst for multi-electron reduction of oxygen. The photocatalyst material includes the tungsten trioxide microparticle carrying on its surface a divalent copper salt, and is exposed to a light having an energy larger than a bandgap energy of the tungsten trioxide. When the photocatalyst material is exposed to the light, electrons in a valence band of tungsten trioxide are photoexcited to a conductor band of the tungsten trioxide, then transferred to Cu (II) ion of divalent copper salt so as to reduce Cu(II) ion to Cu (I) ion. Cu (I) ion performs multi-electron reduction of ambient oxygen atoms, so as to generate hydrogen peroxide by two-electron reduction and water by four-electron reduction. At the same time, Cu (I) ion is oxidized to Cu (II).

:Two-electron reduction

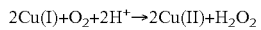

:Four-electron reduction

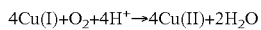

or $3Cu(I)+O_2+4H^+ \rightarrow 2Cu(II)+Cu(III)+2H_2O$

Namely, Cu (II) ion of divalent copper salt carried on tungsten trioxide serves as a catalyst for multi-electron reduction of oxygen.

In the present invention, electrons photoexcited from valence band of tungsten trioxide is efficiently consumed through the above mechanism to produce water and hydrogen peroxide having oxidative activity, thereby overcoming low activity of photoexcited electrons of conventional tungsten trioxide. The photocatalyst material in the present invention exhibits a high efficient oxidative decomposition performance when exposed to visible-light.

Tungsten trioxide has a large electronic potential at its valence band which is comparable to an electronic potential of titanium oxide, and is able to generate strongly oxidative holes when exposed to light. In contrast to the nitrogen-doped titanium oxide in patent reference 1 in which holes generated in isolated level is poorly oxidative, the photocatalyst material in the present invention exhibits a highly efficient oxidative decomposition activity.

The method for decomposition of organic materials in the present invention is characterized by decomposition of organic materials with an aid of the visible light-activated photocatalyst when exposed to visible light.

The photocatalyst material in the present invention has a high oxidative decomposition activity when exposed to visible light, for oxidative decomposition of organic materials in touch with this photocatalyst material.

An interior member in the present invention is characterized in that the interior member has a surface layer impregnated with the visible light-activated photocatalyst material. An air purification device and an apparatus for preparation of oxidizing agents in the present invention are characterized in that they are formed of the visible light-activated photocatalyst material.

The photocatalyst material in the present invention generates highly oxidative holes and hydrogen peroxide which exhibits an oxidative performance in the presence of divalent copper salt, when exposed to visible light having an energy larger than that of a bandgap of tungsten trioxide. Absorption edge wavelength of Tungsten trioxide is about 470 nm. White-light fluorescent lamp generally used in room gives a strong bright line at a wavelength of 400 nm to 450 nm. The photocatalyst material in the present invention exhibits a strong oxidative decomposition activity when exposed to visible-light in such a wavelength region inside a room, although the conventional titanium oxide photocatalyst material exhibits no activity when exposed to the same visible-light.

The conventional titanium oxide photocatalyst has a small electronic potential at the bottom of its conduction band, generating one of reactive oxygen species, superoxide anion ($O_2^-$), by one-electron reduction of ambient oxygen.

:One-electron reduction

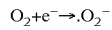

$O_2 + e^- \rightarrow .O_2^-$

The photocatalyst material in the present invention generates photoexcited electrons when exposed to visible light. Then, the generated photoexcited electrons are consumed to yield hydrogen peroxide or water by multi-electron reduction of oxygen via Cu (II) ion. The photocatalyst material of the present invention does not generate one of reactive oxygen, superoxide anion, thereby can be safely used.

Tungsten trioxide not carrying divalent copper salt is caused to be discolored by photochromism accompanied with reduction of W (VI) of tungsten trioxide to W (V), when exposed to light having an energy larger than bandgap of tungsten trioxide. In contrast, the photocatalyst material of the present invention generates photoexcited electrons when exposed to visible light. The generated photoexcited electrons are consumed to perform multi-electrons reduction of oxygen via Cu (II) ion, thereby hardly suffering from discoloration by suppressing the photochromism of tungsten trioxide.

The photocatalyst material of the present invention exhibits a strong oxidative decomposition activity when exposed to visible light, not generating toxic reactive oxygen species, superoxide anion. Besides, this photocatalyst material is free from discoloration by suppressing typical photochromism of tungsten trioxide. Accordingly, the photocatalyst material of the present invention meets requirements for applied to interior member with high visible light-activity, high safety, and invariant appearance, thereby particularly suitable for application to interior members in house. Namely, the interior member having a surface layer impregnated with the visible light-activated photocatalyst of the present invention exhibits a high visible light-activity, high safety, and nice invariant appearance.

The photocatalyst material of the present invention exhibits a strong oxidative decomposition activity when exposed to visible light, thereby suitable for application to the air purification device. Air purification devices utilizing conventional photocatalyst such as titanium oxide necessitate a costly UV-ray source for exhibiting its activity. In contrast, the photocatalyst material of the present invention exhibits a strong oxidative decomposition performance when exposed to light which is emitted from a cheap fluorescent lamp as a light source, allowing air purification devices to be manufactured at a reduced cost.

The photocatalyst material of the present invention generates hydrogen peroxide when exposed to visible light, as described above. Hydrogen peroxide is a stable oxidizing agent and relatively durable. Accordingly, the photocatalyst of the present invention can retain its oxidative decomposition activity for a certain time after photoirradiation is terminated. When the generated hydrogen peroxide is permitted to migrate by a suitable intermediary substance, the photocatalyst material of the present invention can exhibit an oxidative decomposition performance apart from the surface thereof. Accordingly, when manufactured by using the photocatalyst material of the present invention, the apparatus for preparation of oxidizing agents enables it to prepare stable and durable oxidizing agents.

DETAILED DESCRIPTION OF THE INVENTION

Figure 1:
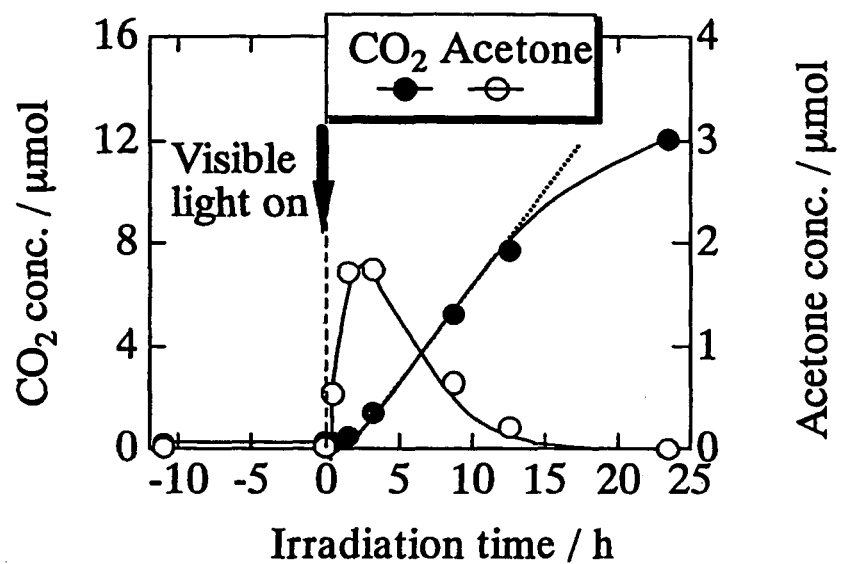
FIG. 1 shows variations in $CO_2$ and acetone concentrations with irradiation time, in Example 1.

Hereafter, explanations are given as to detailed description of the present invention.

The present invention utilizes tungsten trioxide microparticles. The dimension of each tungsten trioxide microparticle is not specifically limited in the present invention. But, tungsten trioxide in the present invention is preferably selected to have a dimension of 1 μm or less, more preferably 500 nm or less. W (VI) of the tungsten trioxide microparticles may be partially reduced to W (V). In view of this, the tungsten trioxide is preferably sintered at a high temperature for oxidization to W (VI) from W (V), for preparation of a photocatalyst material of the present invention.

Each tungsten trioxide microparticle is designed to carry divalent copper salt thereon, for obtaining the photocatalyst material of the present invention. In the present invention, the tungsten trioxide microparticle is not required to carry the divalent copper salt thereon in a particular way, and may be designed to carry the divalent copper salt thereon in various ways, such as solution-infiltration method.

The divalent copper salt carried on tungsten trioxide microparticles preferably has a copper content in a range of 0.0001% to 1% by weight with respect to the tungsten trioxide. The tungsten trioxide needs to be exposed to light so as to be photoexcited in the photocatalyst material of the present invention. As such, the photoirradiation to the tungsten trioxide may be hindered to lower photocatalytic activity when the tungsten trioxide is widely coated with the copper divalent salt. The divalent copper salt serves as a catalyst for multi-electron reduction of oxygen. In view of these, each divalent copper salt carried by tungsten trioxide preferably has a highly dispersive microparticle form not aggregated with each other, for the purpose of efficiently exhibiting its catalytic activity. Accordingly, the carried divalent copper salt preferably has a copper content of 1% or less by weight of tungsten trioxide. But, the divalent copper salt does not sufficiently serve as a catalyst for multi-electron reduction, when the content of the carried divalent copper salt is too low. In view of this, the carried divalent copper salt preferably has a copper content of 0.0001% or more by weight of the tungsten trioxide.

The divalent copper salt in the present invention is preferably composed of hydroxide anion. For example, copper chloride ($CuCl_2.2H_2O$) can be employed as a source of the divalent copper salt in the present invention. In preparation of the photocatalyst material of the present invention, the divalent copper salt are coated on the tungsten trioxide microparticles and then heated in aqueous solution so as to be carried on the surface of each tungsten trioxide microparticle. At the same time, hydroxide ion is generated as anion. The divalent copper salt is presumed to have six-coordinate Cu (II) sites. Specifically, the divalent copper salt is presumably combined with oxygen atom of the tungsten trioxide to form W—O—$Cu(OH)_2.3H_2O$, or adsorbed on the tungsten trioxide to form $Cu(OH)_2.4H_2O$.

The photocatalyst material in the present invention is caused to generate highly oxidative holes and hydrogen peroxide by exposure to visible light having an energy larger than a bandgap of the tungsten trioxide, so as to perform oxidative decomposition of organic materials. The generated hydrogen peroxide is oxidative via divalent copper salt. Absorption edge wavelength of Tungsten trioxide is about 470 nm. White-light fluorescent lamp generally used in room radiates a strong bright line in ca. 400 to 450 nm. Accordingly, the photocatalyst material of the present invention exhibits a strong oxidative decomposition performance when exposed to visible light in room or the like.

The photocatalyst material in the present invention can oxidatively decompose various organic materials, such as aldehydes (e.g., formaldehyde causing sick house syndrome, and acetaldehyde), ketones, volatile organic compound (VOC) (e.g., toluene), odor substances (e.g., methylmercaptan and trimethylamine), sebum, soap scum, oils, contaminants (e.g., seasoning agents), bacteria (e.g., *Bacillus coli* and *Staphylococcus aureus*), and so on. The photocatalyst material in the present invention is utilized for environment cleaning, odor elimination, dirt elimination, sterilization, and so on.

The photocatalyst material in the present invention can be applied to various materials and apparatuses. The photocatalyst material of the present invention exhibits a superior oxidative decomposition performance when exposed to UV-light as well as visible light, and can be suitably applied to various members as conventional photocatalyst material being applied to. Particularly, the photocatalyst material of the present invention can be suitably applied to fabrication of interior members and air purification devices.

As described above, the photocatalyst material of the present invention exhibits a strong oxidative decomposition performance by exposure to visible light, and does not generate toxic reactive oxygen species such as superoxide anion. Besides, the photocatalyst material of the present invention is free from discoloration by suppressing typical photochromism of the tungsten trioxide. The photocatalyst material of the present invention meets requirements for application to fabrication of interior members in house in view of visible light-activity, safety, and invariant appearance, thereby being suitable particularly to interior members in house.

The photocatalyst material of the present invention can be impregnated into a surface layer of interior members, for application to the interior members. This photocatalyst material can be impregnated into the surface layer of interior members in various ways. For example, the surface layer of interior members can be impregnated with this photocatalyst material by applying a coating material mixed with this photocatalyst material on a surface of the interior member.

The interior member impregnated at its exterior layer with the photocatalyst material can be applied to doors, storage doors, ceiling materials, wall materials, floor materials, partitions, decorative materials, steps, stiles, hand rails, window frames, wash stands, kitchen, toilet, bathroom member, and so on.

As described above, the photocatalyst material in the present invention exhibits a strong oxidative decomposition activity when exposed to visible light, thereby being suitably applied to an air purification device. The conventional air purification device utilizing photocatalyst of titanium oxide necessitates a costly UV-light source for exhibiting its activity. In contrast, the air purification device utilizing the photocatalyst material of the present invention exhibits a strong oxidative decomposition activity when exposed to light which is radiated from a light source of cheap luminescent lamp, allowing the air purification device to be manufactured at a reduced cost.

The photocatalyst material of the present invention can be applied to manufacture of the air purification device in various ways. For example, the photocatalyst material is supported to filters filtering air, and then the filters are assembled into the air purification device.

As described above, the photocatalyst material of the present invention is characterized by generation of hydrogen peroxide when exposed to visible light. Hydrogen peroxide is stable as an oxidizing agent, and relatively durable. The photocatalyst of the present invention can retain its oxidative decomposition activity for a certain time even after photoirradiation is terminated. When the generated hydrogen peroxide is permitted to migrate by a suitable intermediary substance, this photocatalyst material of the present invention can exhibit the oxidative decomposition performance apart from the surface of this photocatalyst material. Accordingly, the photocatalyst material of the present invention can be applied to manufacture of apparatus for preparation of oxidizing agents.

The photocatalyst material in the present invention can be applied to the apparatus for preparation of oxidizing agents in various ways. For example, the members supporting the photocatalyst material of the present invention can be combined with a light source, in order to manufacture the apparatus for preparation of oxidizing agents. This apparatus for preparation of oxidizing agents can be assembled into a washing machine, so as to generate hydrogen peroxide from water in a washing tank of the washing machine for decomposition of dirt and odor in the washing tank by oxidative decomposition performance of the generated hydrogen peroxide.

EXAMPLE

Explanations are specifically given with reference to Examples of the present invention. The present invention is not limited to the following Examples.

Example 1

$WO_3$ powder (a mean particle diameter: 250 nm, available from Kojundo Chemical Laboratory Co., Ltd,) were filtered to eliminate particles each having a diameter of 1 µm or more, and then sintered for three hours at 650° C. in advance, in order to obtain tungsten trioxide microparticles.

The obtained tungsten trioxide microparticles was suspended in a distilled water (10% by weight: $WO_3$ vs. $H_2O$). Next, 0.1 percent by weight (Cu(II) vs. $WO_3$) of $CuCl_2. 2H_2O$ (available form Wako Pure Chemical Industries, Ltd.) was added to the suspension, then heated up to 90° C. while stirred, and subsequently retained for one hour. Next, the obtained suspension was filtered by means of a suction filtration. Then, the obtained residue was washed with a distilled water, and subsequently heat-dried at 110° C., so as to obtain a sample of tungsten trioxide microparticles each carrying on its surface a divalent copper salt.

The obtained tungsten trioxide microparticles carrying divalent copper salt were subjected to analyses by using inductively-coupled plasma emission spectrometry (ICP-AES, P-4010, available from Hitachi Co. Ltd.) and polarized Zeeman atomic absorption analysis (Polarized Zeeman AAS, Z-2000, available from Hitachi Co. Ltd.), for obtaining a copper (II) content of divalent copper salt carried on the tungsten trioxide microparticle. The copper (II) content of divalent copper salt carried on the tungsten trioxide microparticle is determined to be 0.0050% by weight (Cu (II) vs. $WO_3$: 5% by weight of initial amount).

Example 2

A sample of the tungsten trioxide microparticle carrying thereon divalent copper salt was obtained in almost the same way as in Example 1. But, $WO_3$ powder was not sintered in advance, in order to obtain the sample of tungsten trioxide microparticle in this example.

Comparative Example 1

$WO_3$ powder (a mean particle diameter: 250 nm, available from Kojundo Chemical Laboratory Co., Ltd,) was filtered to eliminate particles each having a diameter of 1 µm or more, and then sintered for three hours at 650° C. in advance, in order to obtain a sample of tungsten trioxide microparticles.

Comparative Example 2

Anatase-form titanium oxide (ST-01, available from Ishihara Sangyo kaisha, Ltd.) was annealed at 550° C. for three hours to obtain a sample of nitrogen-doped titanium oxide microparticles.

Comparative Example 3

The divalent copper salt was carried on rutile form of $TiO_2$ powder (MT-150A, TAYCA Co. Ltd.), instead of tungsten trioxide microparticles, in almost the same way as in Example 1, in order to obtain a sample of titanium oxide microparticles carrying thereon the divalent copper salt.

(Property Evaluation)

The samples of Examples 1 to 2 and Comparative examples 1 to 3 were evaluated in terms of their photocatalytic activities, through determination of concentrations of acetone and $CO_2$ which are generated by vapor-phase oxidative decomposition of 2-propanol (IPA) by exposure to visible light. The evaluation is described below in detail.

First, 300 mg of each sample was uniformly spread on a petri dish (area: 5.51 cm$^2$) having an inner diameter of 26.5 mm, and then encapsulated into a quartz vessel having a capacity of 500 ml. Next, this vessel was supplied with synthetic air, and exposed to all-optic Xe-lamp (Luminar Ace 251, available from Hayashi watch-works Co., Ltd.) to decompose a residual organic substances on a surface of each sample. After generation of $CO_2$ from the residual organic substance was confirmed to stop, the vessel was supplied again with synthetic air.

Reactive IPA gas was passed through dried nitrogen gas, and then collected as vaporized IPA inside a tedra pack. The vessel containing the synthetic air was supplied with 300 ppmv (6.1 µmol) of the collected IPA gas. Next, the vessel was kept in dark place. Later, the supplied IPA was caused to adsorb onto the surface of each sample, which had been observed for 10 hours for confirmation of adsorption equilibrium. After the adsorption equilibrium was confirmed, the sample was irradiated with light having a wavelength of 400 nm to 530 nm, which was emitted from Xe-lamp toward an upper portion of the vessel and filtered through a glass filter (L-42, B-47, C-40C, AGC Techno glass Co., Ltd). Gases inside the vessel were sampled at predetermined time intervals during photoirradiation, for determination of concentration of IPA as well as concentrations of acetone and $CO_2$ which are generated by decomposition of IPA by means of hydrogen flame ionization gas chromatography (GC-8A, Shimadzu Corporation). The generated $CO_2$ is methanated via Ni catalyst in the presence of hydrogen to determine the concentration of $CO_2$ by Methanizer (MT-N, Shimadzu Corporation). The intensity of irradiated light is measured for each wavelength by means of spectral irradiance illuminance meter (USR-30V, Ushio inc.), and controlled to be $1.00 \times 10^3$ mW cm$^{-2}$. The number of photon (the number of absorbed photon per unit time) is obtained by multiplying an absorption ratio (1-reflectance) by irradiated area (area of the petri dish: 5.51 cm$^2$). The absorption ratio is obtained from a UV-visible diffuse spectrum for each sample.

FIG. 1 shows variations in acetone and $CO_2$ concentrations with the irradiation time, which result from IPA vapor-phase decomposition of the sample of Example 1. FIG. 1 demonstrates the generation and decomposition of acetone, and generation of $CO_2$ via induction period. The quantum efficiency is determined to be 0.17%, based on gradient of a dotted line showing the variation in $CO_2$ concentration in FIG. 1. The turnover number with respect to Cu (II) content is 50 or more. IPA is presumed to be catalytically decomposed into $CO_2$ while being exposed to visible light.

In contrast, $WO_3$ not carrying Cu (II) ion in the sample of Comparative example 1 was revealed to generate only a small amount of acetone and no amount of $CO_2$, by IPA decomposition in the same way as in Examples. Accordingly, $WO_3$ is required to carry Cu (II) ion for exhibiting a high visible light activity.

The quantum yield and the turnover number were determined in accordance with the following ways.

With respect to quantum efficiency, absorption of 18 photons is presumably required for decomposition of one molecule of IPA into three molecules of $CO_2$. ($C_3H_8O + 5H_2O + 18H^+ \rightarrow 3CO_2 + 18H^+$). Namely, the quantum efficiency (QE) due to the generation of $CO_2$ is expressed as QE=6×$CO_2$ generation rate/the number of absorbed photons. The quantum efficiency (QE) in Example 1 is determined to be 17%, based on the following formula.

$$\text{Quantum efficiency (QE)} = 6 \times 1.9 \times 10^{-10} \text{ molsec}^{-1} \times 6.0 \times 10^{23} \text{ quanta·mol}^{-1} / (5.5 \text{ cm}^2 \times 7.1 \times 10^{14} \text{ quanta·cm}^{-2} \cdot \text{sec}^{-1}) = 1.7 \times 10^{-1} (=17\%)$$

With respect to the turnover number, the sample of Example 1 contains 300 mg of Cu(II)$WO_3$ and 0.005% by weight of Cu(II) ion. Accordingly, the content of Cu(II) ion carried on $WO_3$ is 0.015 mg, i.e., 0.24 mol. The content of generated $CO_2$ for 1.5 days is determined to be 12.2 mol, thereby turnover number in Example 1 is fifty-one (12.2 mol/0.24 mol=51).

Table 1 shows the number of absorbed photons, $CO_2$ generation rate, and quantum efficiency with respect to Examples 1 and 2, and Comparative examples 1 to 3.

TABLE 1

| | The number of absorbed photon (quanta·cm$^{-2}$·sec$^{-1}$) | $CO_2$ generation rate (mol·sec$^{-1}$) | Quantum efficiency (%) |
|---|---|---|---|
| Example 1 Cu(II)/WO$_3$ sintered | $7.1 \times 10^{14}$ | $1.9 \times 10^{-10}$ | 17 |
| Example 2 Cu(II)/WO$_3$ Not sintered | $6.6 \times 10^{14}$ | $8.3 \times 10^{-11}$ | 8.3 |
| Comparative example 1 WO$_3$ | $7.3 \times 10^{14}$ | N.D. | N.D. |
| Comparative example 2 N-doped TiO$_2$ | $4.9 \times 10^{14}$ | $1.2 \times 10^{-11}$ | 1.6 |
| Comparative example 3 Cu(II)/TiO$_2$ | $1.8 \times 10^{14}$ | $2.5 \times 10^{-11}$ | 8.8 |

According to Table 1, the photocatalyst materials in Examples of the present invention was revealed to exhibit much better performance than conventional photocatalyst materials in the comparative examples.

Figure 2A:
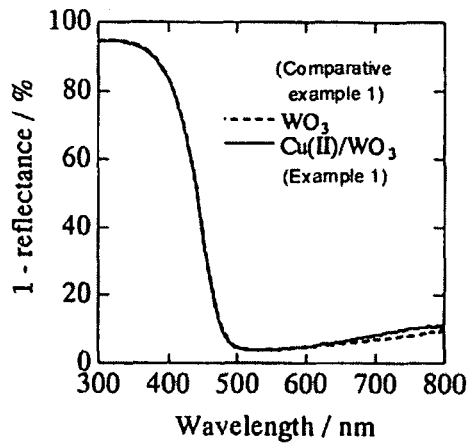
FIGS. 2A, 2B, and 2C show UV-visible diffuse spectra.
Figure 2B:
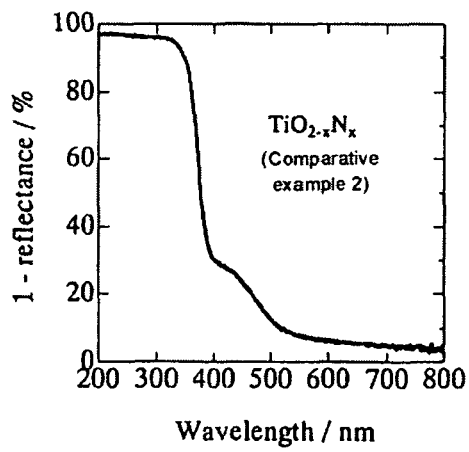
Figure 2C:
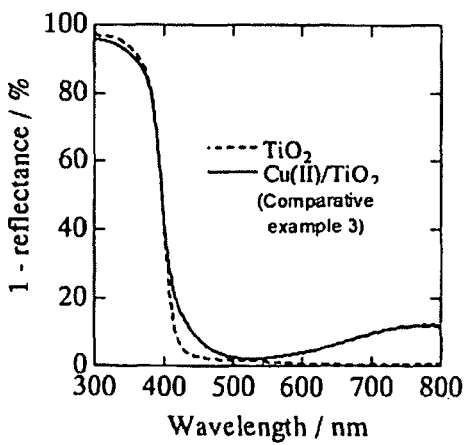

Cu(II)/WO$_3$ in Example 1 exhibits a doubled quantum efficiency with respect to Cu(II)/TiO$_2$ in Comparative example 3, revealing that Cu(II)/WO$_3$ in Example 1 serves a significantly improved light usage efficiency. With respect to $CO_2$ generation rate (=photo absorption efficiency×quantum efficiency) related to photocatalytic activity, it is noteworthy that Cu(II)/WO$_3$ in Example 1 exhibits 8-fold $CO_2$ generation rate with respect to Cu(II)/TiO$_2$ in Comparative example 3. As shown in Table 1 and FIG. 2A, FIG. 2B, and FIG. 2C, Cu(II)/WO$_3$ can absorb the visible light via interband transition. In contrast, Cu(II)/TiO$_2$ can not absorb the visible light via interband transition, giving only a small photoabsorption.

Cu(II)/WO$_3$ in Example 1 exhibits 16-fold $CO_2$ generation rate (=photo-absorption efficiency×quantum efficiency) with respect to nitrogen-doped titanium oxide in Comparative example 2 which is a typical conventional visible light-active photocatalyst material. This is due to the fact that Cu(II)/WO$_3$ absorbs the visible light via interband transition, while nitrogen-doped titanium oxide absorbs the visible light only via a transition involving isolated energy level of nitrogen. Besides, Cu(II)/WO$_3$ exhibits a large amount of photoabsorption, while nitrogen-doped titanium oxide has a high electronic potential of the isolated energy level and generates poorly oxidizing holes. Since a valence band of WO$_3$ has a low electronic potential, the holes generated in valence band of Cu(II)/WO$_3$ exhibit a significantly strong oxidizing performance.

The invention claimed is:

1. A visible light-activated photocatalyst material comprising a tungsten trioxide microparticle carrying on its surface a divalent copper salt, wherein said divalent copper salt is composed of hydroxide anion.

2. A method for decomposition of an organic material comprising a step of irradiating visible light to said visible light-activated photocatalyst material as set forth in claim 1 to decompose the organic material.

3. An interior member having a surface layer impregnated with said visible light-activated photocatalyst material as set forth in claim 1.

4. An air purification device being formed of said visible light-activated photocatalyst material as set forth in claim 1.

5. An apparatus for preparation of an oxidizing agent being formed of said visible light-activated photocatalyst material as set forth in claim 1.

6. The visible light-activated photocatalyst material as set forth in claim 1, wherein said divalent copper salt carried on said tungsten trioxide has a copper content of 0.0001% to 1% by weight of said tungsten trioxide.

7. A method for decomposition of an organic material comprising a step of irradiating visible light to said visible light-activated photocatalyst material as set forth in claim 6 to decompose the organic material.

8. An interior member having a surface layer impregnated with said visible light-activated photocatalyst material as set forth in claim 6.

9. An air purification device being formed of said visible light-activated photocatalyst material as set forth in claim 6.

10. An apparatus for preparation of an oxidizing agent being formed of said visible light-activated photocatalyst material as set forth in claim 6.

* * * * *